United States Patent
Yang et al.

(10) Patent No.: US 6,632,028 B1
(45) Date of Patent: Oct. 14, 2003

(54) APPARATUS AND METHOD FOR ALIGNING AN OPTICAL FIBER WITH AN OPTICAL DEVICE

(75) Inventors: Renyi Yang, Goleta, CA (US); Thomas Reynolds, Ventura, CA (US); Robert A. Craven, Santa Barbara, CA (US); Aaron Hawkins, West Lake Village, CA (US)

(73) Assignee: VTR Optoelectronics, Inc., Santa Barbara, CA (US)

( * ) Notice: Subject to any disclaimer, the term of this patent is extended or adjusted under 35 U.S.C. 154(b) by 0 days.

(21) Appl. No.: 09/938,389

(22) Filed: Aug. 24, 2001

Related U.S. Application Data
(60) Provisional application No. 60/227,818, filed on Aug. 25, 2000.

(51) Int. Cl.$^7$ ................................................. G02B 6/36
(52) U.S. Cl. ........................................ 385/88; 257/782
(58) Field of Search .......................... 385/88, 90, 91, 385/92, 89; 257/782, 783

(56) References Cited

U.S. PATENT DOCUMENTS

| | | | | |
|---|---|---|---|---|
| 5,559,918 A | * | 9/1996 | Furuyama et al. | ............ 385/92 |
| 5,881,198 A | * | 3/1999 | Haake | ......................... 385/136 |
| 6,205,264 B1 | * | 3/2001 | Jin et al. | ....................... 385/14 |
| 6,238,100 B1 | * | 5/2001 | Sasaki et al. | .................. 385/59 |

\* cited by examiner

Primary Examiner—Michael C. Zarroli
(74) Attorney, Agent, or Firm—Hogan & Hartson, LLP (57) ABSTRACT

An apparatus and method for aligning an optical fiber with an optical device having bond pads attached thereto. The apparatus includes a fiber mount assembly having a body portion with an opening provided therein to receive the optical fiber, and two leg portions integrally connecting to and extending from the body portion. Bond pads are also attached to the two leg portions. The apparatus further includes an optical device mount assembly having bond pads attached thereto, and a plurality of eutectic solder bumps provided on the bond pads. The eutectic solder bumps connect the bond pads of the optical device and the two leg portions of the fiber mount assembly to the bond pads of the optical device mount assembly. The concentration of a component of the eutectic material in the solder bumps is increased, via a reaction between the bond pads and the solder bumps, until the eutectic material hardens and rigidly connects the bond pads of the optical device and the two leg portions of the fiber mount assembly to the bond pads of the optical device mount assembly, aligning the optical fiber with the optical device.

12 Claims, 7 Drawing Sheets

APPARATUS AND METHOD FOR ALIGNING AN OPTICAL FIBER WITH AN OPTICAL DEVICE

CROSS REFERENCE TO RELATED APPLICATION

The present application claims the benefit of the filing date of U.S. Provisional Application No. 60/227,818, filed Aug. 25, 2000, the teachings of which are incorporated herein by reference.

BACKGROUND OF THE INVENTION

A. Field of the Invention

The present invention relates generally to optical fibers, and, more particularly to an apparatus and method for aligning an optical fiber with a optical device.

B. Description of the Related Art

Optical devices such as photodiodes, are used in optical communication systems for absorbing and converting light from an optical fiber into an electrical current signal. It is important, particularly in the optical communications field, to provide low loss couplings between an optical component and an optical fiber. Such low loss couplings are generally achieved by positioning the optical component in accurate alignment with the optical fiber, ideally within 0.1 micron both horizontally and vertically of the desired alignment. Unfortunately, the known methods of achieving such accurate alignment are either difficult to implement or require expensive, high-tolerance components.

SUMMARY OF THE INVENTION

An object of the invention is to provide an apparatus and method for aligning an optical fiber with an optical device that overcomes the problems of the related art.

A further object of the invention is to provide an apparatus and method for aligning an optical fiber with an optical device that consistently and accurately aligns the optical fiber with the optical device.

Additional objects and advantages of the invention will be set forth in part in the description which follows, and in part will be learned from the description, or may be learned by practice of the invention. The objects and advantages of the invention will be realized and attained by means of the elements and combinations particularly pointed out in the appended claims.

To achieve the objects and in accordance with the purpose of the invention, as embodied and broadly described herein, the invention comprises an apparatus for aligning an optical fiber with an optical device having a first plurality of bond pads provided thereon, the apparatus including: a fiber mount assembly having a body portion with an opening provided therein to receive the optical fiber, and two leg portions integrally connecting to and extending from the body portion, the two leg portions having a second plurality of bond pads provided thereon; and an optical device mount assembly having a third plurality of bond pads provided thereon, and a plurality of eutectic solder bumps provided on the third plurality of bond pads for connecting the first plurality of bond pads of the optical device and the second plurality of bond pads of the two leg portions of the fiber mount assembly to the optical device mount assembly, wherein the concentration of a component of the eutectic material in the plurality of eutectic solder bumps is increased, via a reaction between the first, second and third pluralities of bond pads and the plurality of eutectic solder bumps, until the eutectic material hardens and rigidly connects the first plurality of bond pads of the optical device and second plurality of bond pads of the two leg portions of the fiber mount assembly to the third plurality of bond pads of the optical device mount assembly, aligning the optical fiber with the optical device.

To further achieve the objects and in accordance with the purpose of the present invention, the invention comprises a method for aligning an optical fiber with an optical device, the method including the steps of: providing a plurality of eutectic solder bumps on a first plurality of bond pads provided on an optical device mount assembly; contacting a second plurality of bond pads provided on two leg portions of a fiber mount assembly with some of the plurality of eutectic solder bumps, the fiber mount assembly having a body portion with an opening provided therein, wherein the two leg portions integrally connect to and extend from the body portion; contacting a third plurality of bond pads provided on the optical device with the remaining plurality of eutectic solder bumps provided on the first plurality of bond pads of the optical device mount assembly; increasing the concentration of a component of the eutectic material in the plurality of eutectic solder bumps, via a reaction between the first, second and third pluralities of bond pads and the plurality of eutectic solder bumps, until the eutectic material hardens and rigidly connects the third plurality of bond pads of the optical device and the second plurality of bond pads of the two leg portions of the fiber mount assembly to the first plurality of bond pads of the optical device mount assembly, aligning the optical fiber with the optical device; and providing the optical fiber through the opening provided in the body portion of the fiber mount assembly.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate one embodiment of the invention and together with the description, serve to explain the principles of the invention. In the drawings.

DESCRIPTION OF THE PREFERRED EMBODIMENT

Reference will now be made in detail to the present preferred embodiment of the invention, an example of which is illustrated in the accompanying drawings. Wherever possible, the same reference numbers will be used throughout the drawings to refer to the same or like parts.

Figure 1:
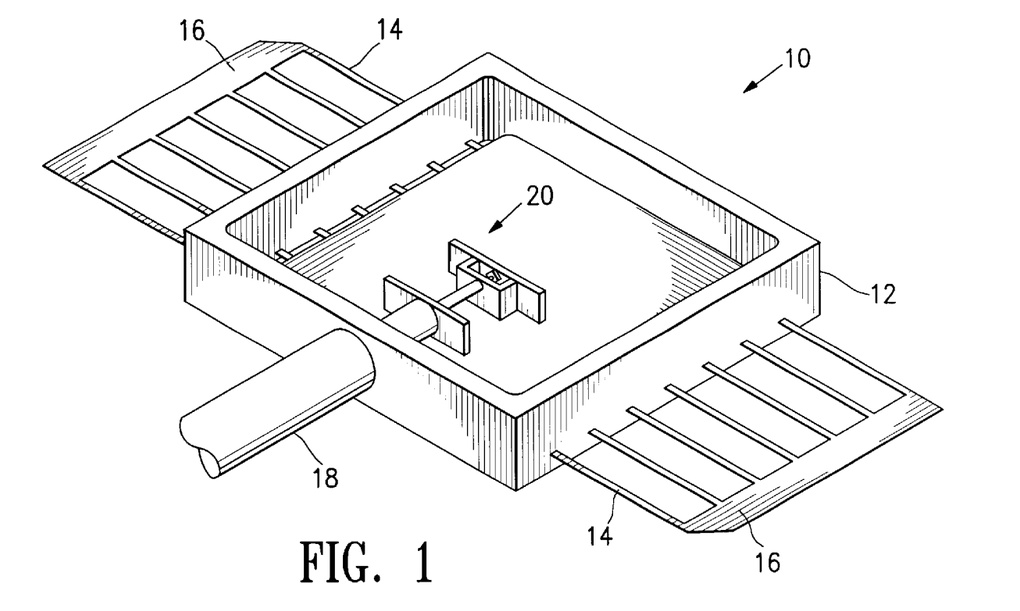
FIG. 1 is an isometric view showing an apparatus for aligning an optical fiber with an optical device in accordance with a preferred embodiment of the present invention.

In accordance with the invention, the present invention is broadly drawn to an apparatus and method for aligning an optical fiber with an optical device. As shown in FIG. 1, the aligning apparatus 20 of the present invention is housed in a metal package 10 that includes a housing 12 having a plurality of support arms 14 connecting to and extending from housing side walls. Support arms 14 connect to mounting fixtures 16. Mounting fixtures 16 enable metal package 10, via support arms 14, to be affixed within an optical communications system (not shown). Aligning apparatus 20 is provided in a recessed portion of housing 12 of metal package 10 and may connect to additional electronic components (not shown) provided in the recessed portion of housing 12. Finally, an optical fiber cable 18 is provided through a side wall of housing 12 adjacent to aligning apparatus 20.

Figure 2:
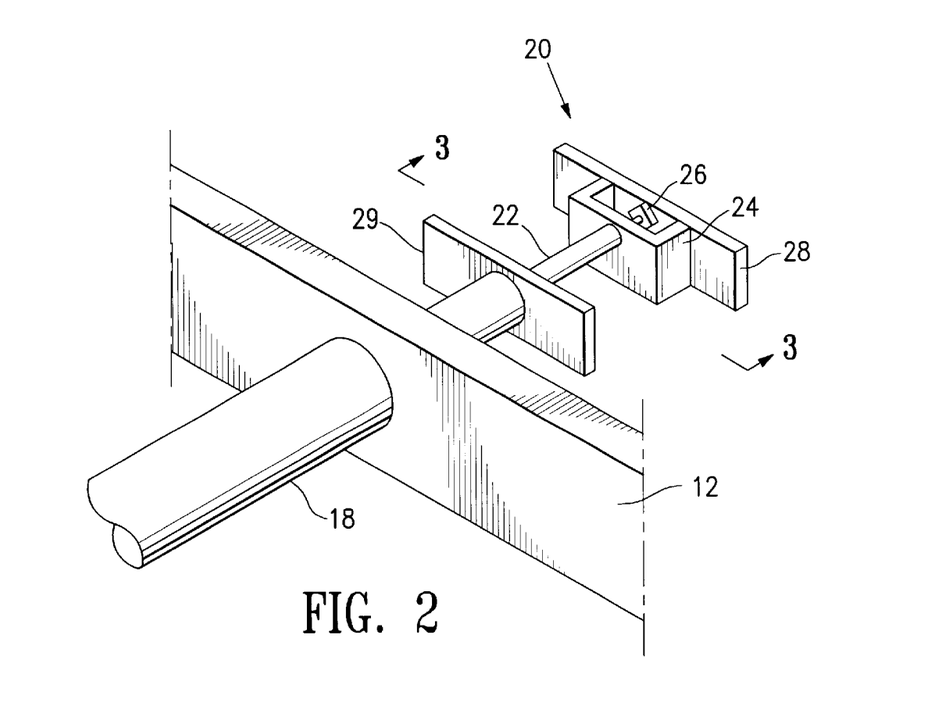
FIG. 2 is an exploded isometric view showing a portion of the preferred embodiment shown in FIG. 1.

As embodied herein and as shown in the exploded isometric view of FIG. 2, aligning apparatus 20 comprises a fiber mount assembly 24 that connects to an optical device mount assembly 28. An optical fiber 22 from optical fiber cable 18 is provided through an opening 38 (shown in FIG. 4(a)) formed in fiber mount assembly 24. Fiber mount assembly 24 aligns optical fiber 22 with an optical device 26 connected to optical device mount assembly 28.

Preferably, optical device 26 comprises an avalanche photodiode having a silicon multiplication and an InGaAs absorption region, as described in a U.S. patent application filed the same day as the present application Ser. No. 09/551,140, filed Jul. 17, 2000 (inventor Aaron Hawkins) and assigned to the Assignee of the present invention, Ciena Corporation. However, depending upon the optical communications application, optical device 26 may comprise other similar photoelectric conversion devices known in the art, such as, for example, a laser diode or a PIN photodiode.

Figure 3:
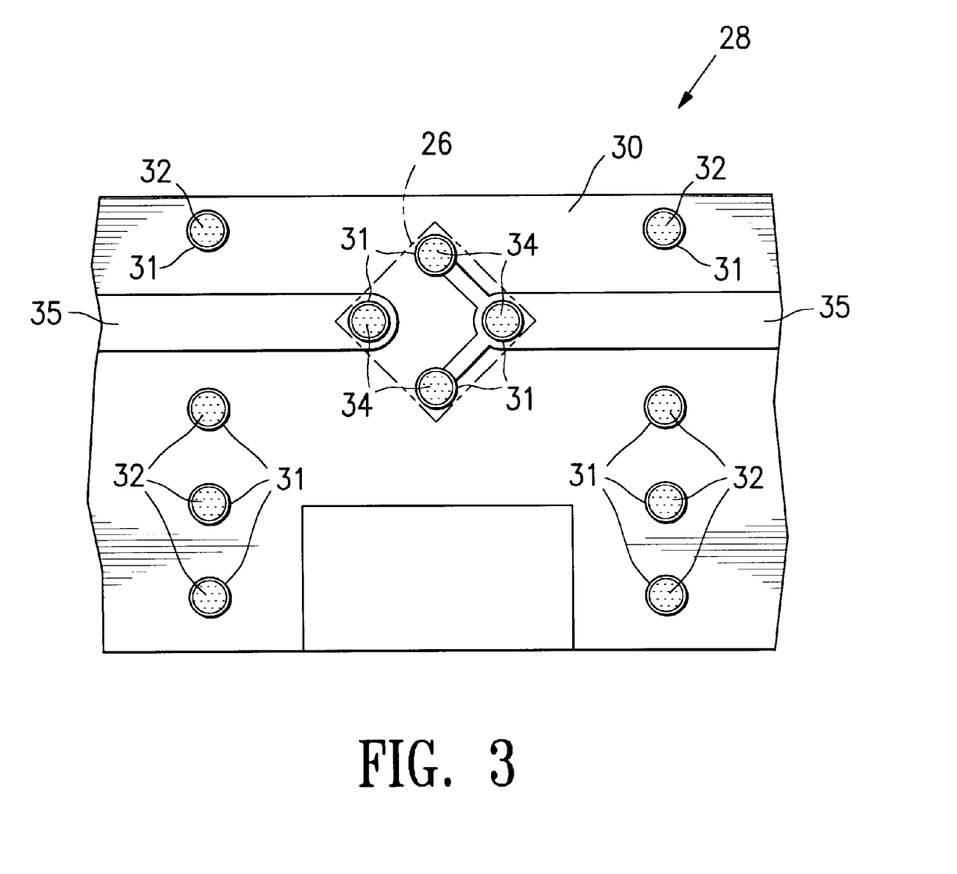
FIG. 3 is a front view (taken in the direction of line 3—3 of FIG. 2) showing a portion of an optical device mount assembly of the preferred embodiment of the present invention.

FIG. 3 is front view (taken in the direction of line 3—3 of FIG. 2 with the fiber mount assembly removed for clarity) of a portion of optical device mount assembly 28. Optical device mount assembly 28 includes a body portion 30 having a plurality of bond pads 31 and conductor lines 35 provided thereon. Bond pads 31 of optical device mount assembly 28 are precisely located on optical device mount assembly 28 using conventional photolithography techniques. Solder bumps 32 connect fiber mount assembly 24 to optical device mount assembly 28, whereas solder bumps 34 connect optical device 26 to optical device mount assembly 28. Conductor lines 35 electrically connect optical device 26, via bond pads 31 located thereunder, to other components contained in metal package 10, and may be made from a conductive metal known in the art.

Figure 4A:
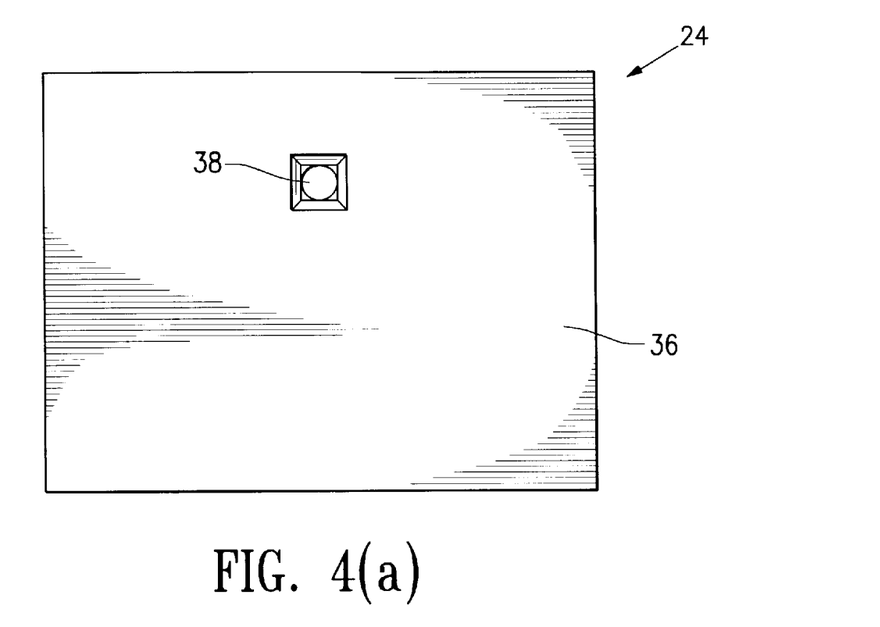
FIG. 4(a) is a front view (also taken in the direction of line 3—3 of FIG. 2) showing a fiber mount assembly of the preferred embodiment of the present invention.
Figure 4B:
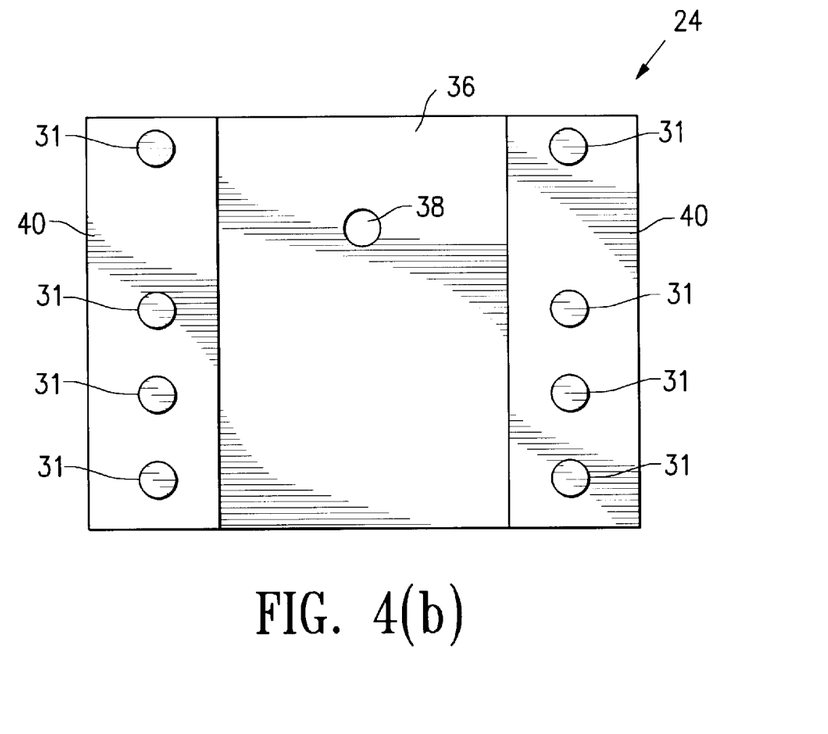
FIG. 4(b) is a back view of the fiber mount assembly shown in FIG. 4(a)

FIGS. 4(a) and 4(b) are front and back views, respectively, (also taken in the direction of line 3—3 of FIG. 2) showing fiber mount assembly 24. As shown, fiber mount assembly 24 comprises a body portion 36 with an opening 38 provided therein for receiving optical fiber 22, and two leg portions 40 integrally connecting to and extending from body portion 36. The two leg portions 40 of fiber mount assembly 24 connect to optical device mount assembly 28, via solder bumps 32 provided between bond pads 31 of optical device mount assembly 28 and bond pads 31 provided on two leg portions 40 of fiber mount assembly 24. The locations of bond pads 31 of fiber mount assembly 24, with respect to the location of opening 38 and bond pads 31 of optical device mount assembly 28, are formed through conventional silicon micro-machining fabrication.

Bond pads 31 are also provided on a surface of optical device 26. The locations of bond pads 31 of optical device 26 with respect to the active absorption region 42 (see FIG. 5(c)) of optical device 26 are precisely defined during fabrication of optical device 26.

Preferably, bond pads 31 of optical device 26, fiber mount assembly 24 and optical device mount assembly 28 comprise a titanium/platinum/gold (Ti/Pt/Au) alloy, but other materials may be selected depending upon the material selected for solder bumps 32, 34. The Ti/Pt/Au alloy of bond pads 31 preferably comprises a one-thousand angstrom thick layer of titanium (Ti), a two-thousand angstrom thick layer of platinum (Pt), and a five-thousand angstrom thick layer of gold (Au). The thickness of the gold layer provided in bond pads 31 is critical to proper alignment of optical device 26 with optical fiber 22 since the gold in bond pads 31 increases the concentration of the gold in solder bumps 32, 34, hardening solder bumps 32, 34, as discussed below.

Figure 6:
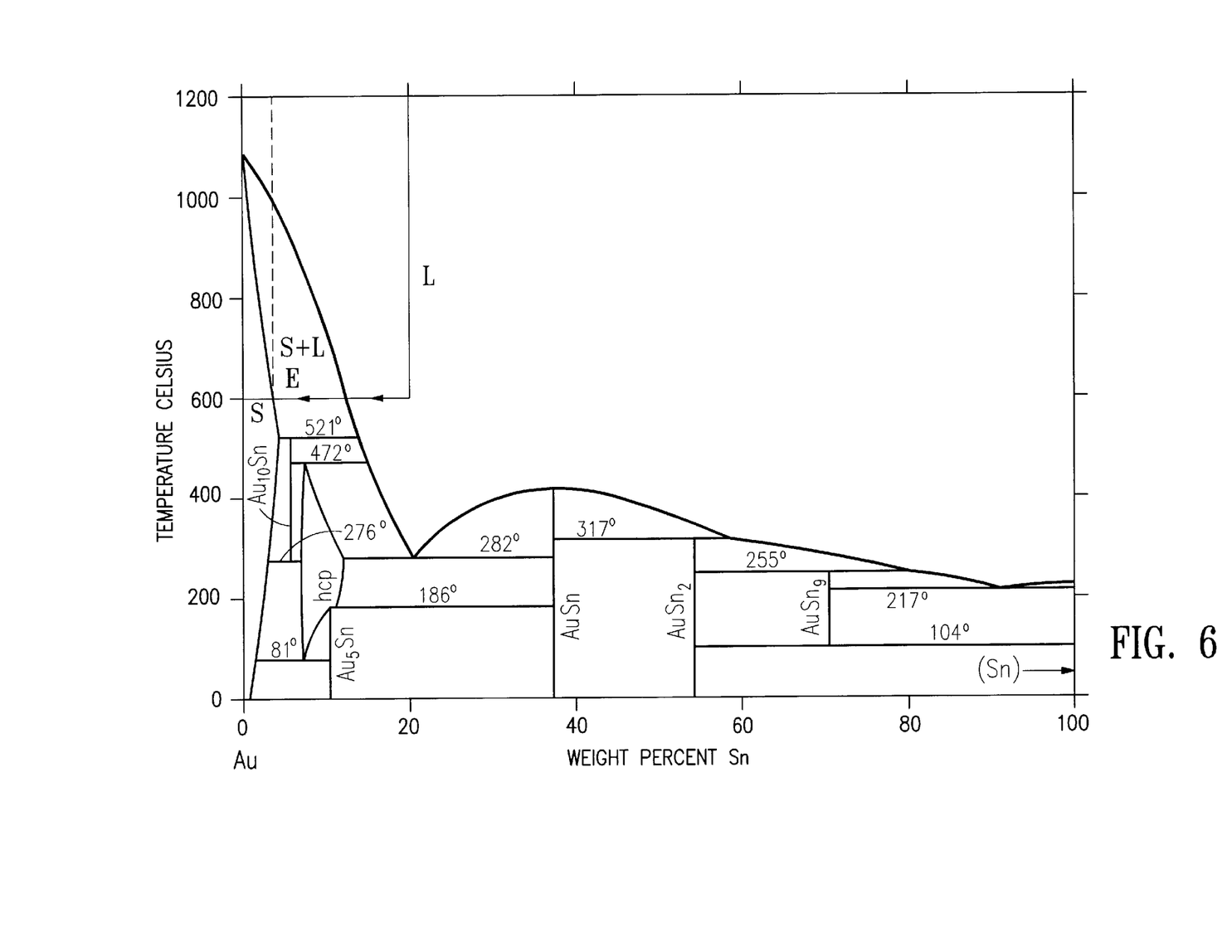
FIG. 6 is a graph showing the eutectic properties of the solder bumps used to connect and align the fiber mount assembly to the optical device mount assembly of the preferred embodiment of the present invention.

Solder bumps 32, 34 preferably comprise a eutectic material such as a gold/tin (Au/Sn) alloy having a gold concentration of eighty percent by weight and a tin concentration of twenty percent by weight, but other eutectic materials may be used. A eutectic material is a material that has a specific concentration at certain temperatures. FIG. 6 is a graph showing the eutectic properties of the Au/Sn alloy used for solder bumps 32, 34 of the present invention. As shown in FIG. 6, as the concentration of gold (Au) is increased in the Au/Sn alloy and the temperature remains constant at a temperature $T_E$ of 800 EC, the concentration of tin (Sn) will decrease and the Au/Sn alloy will pass from the liquid (L) phase into the solid (S) and liquid (L) phase. This will occur until the gold concentration reaches point E where the Au/Sn alloy passes from the solid (S) and liquid (L) phase into the solid (S) phase and hardens. At a temperature $T_E$ of 800 EC, for example, this occurs when the concentration of gold (Au) in the Au/Sn alloy reaches approximately ninety-seven percent by weight. After point E, as the concentration of gold (Au) is increased in the Au/Sn alloy, the Au/Sn alloy remains in the solid (S) phase at a temperature $T_E$ of 800 EC.

Figure 5A:
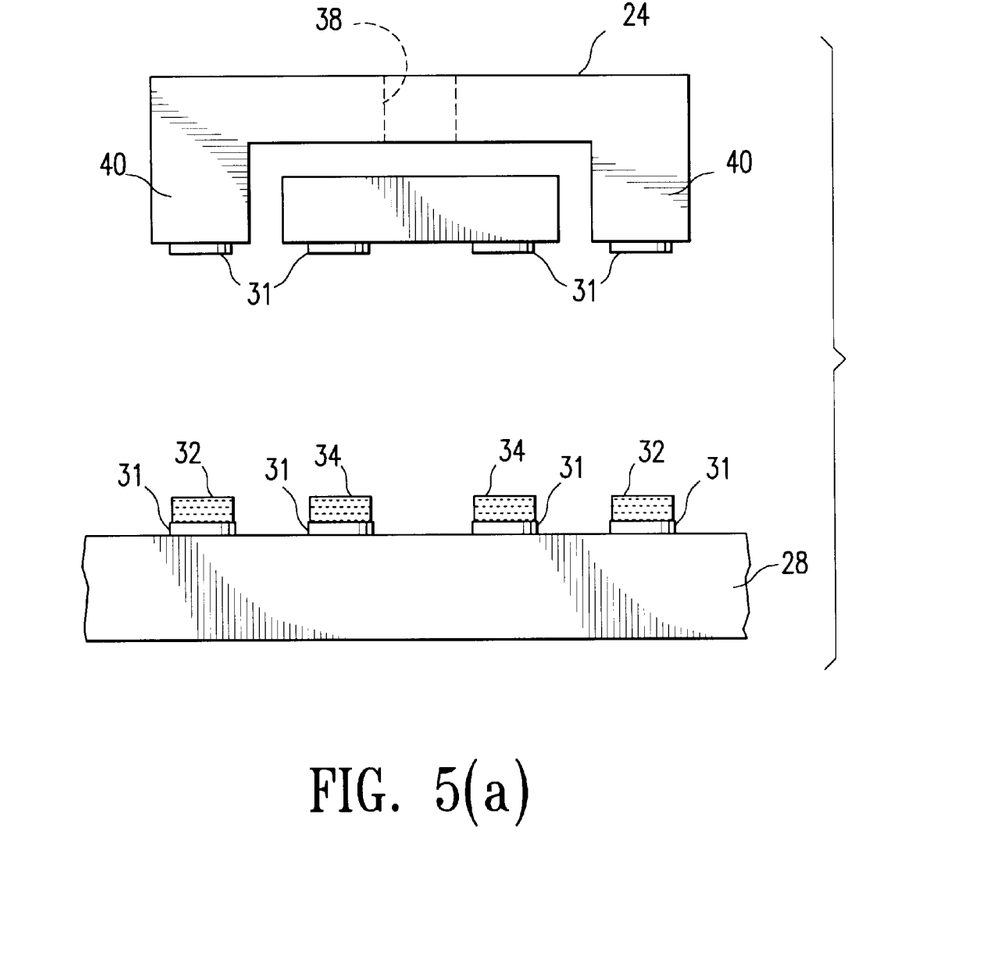
FIG. 5(a) is an exploded top view of the exploded portion shown in FIG. 2 and showing the initial connection, via liquid solder bumps, of the optical device and fiber mount assembly to the optical device mount assembly.
Figure 5B:
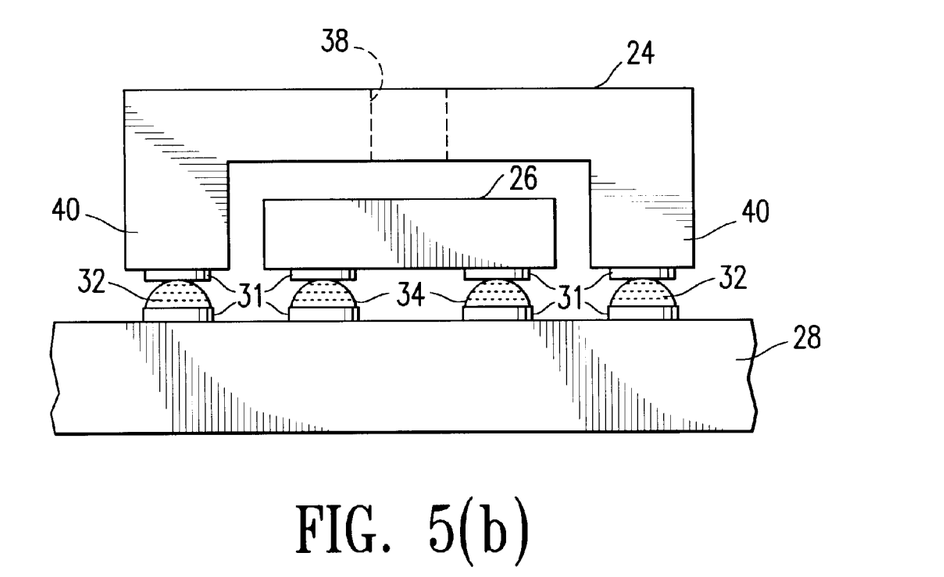
FIG. 5(b) is an exploded top view of the exploded portion shown in FIG. 2 and showing the solder connection during reflow (the solid and liquid phase) of the solder bumps.

In addition to the prior steps shown above, the method of mounting fiber mount assembly 24 and optical device 26 to optical device mount assembly 28 comprises the following steps. As shown in FIG. 5(a), liquid Au/Sn alloy solder bumps 32, 34 (having a gold concentration of at least eighty percent by weight) are applied to bond pads 31 of optical device mount assembly 28, while maintaining a constant temperature. While Au/Sn alloy solder bumps 32, 34 are still in their liquid phase, bond pads 31 of two legs 40 of fiber mount assembly 24 are placed in contact with Au/Sn solder bumps 32, while bond pads 31 of optical device 26 are placed in contact with Au/Sn solder bumps 34. The gold from bond pads 31 of optical device 26, fiber mount assembly 24 and optical device mount assembly 28 reacts with and increases the concentration of a component of the liquid eutectic solder bumps 32, 34, namely gold. In particular, gold in the bond pads dissolves into the solder bumps to thereby increase the concentration of gold in Au/Sn alloy solder bumps 32, 34. As the Au/Sn alloy solder bumps 32, 34 begin to solidify, because of the increased gold concentration, the surface tension of the liquid Au/Sn alloy solder bumps 32, 34 forces bond pads 31 of two legs 40 of fiber mount assembly 24 and bond pads 31 of optical device 26 into proper alignment with bond pads 31 of optical device mount assembly 28 since this where the lowest amount of surface tension of the liquid Au/Sn alloy solder bumps 32, 34 is found. Au/Sn alloy solder bumps 32, 34 eventually solidify and affix fiber mount assembly 24 and optical device 26 to optical device mount assembly 28, as shown in FIG. 5(c).

Figure 5C:
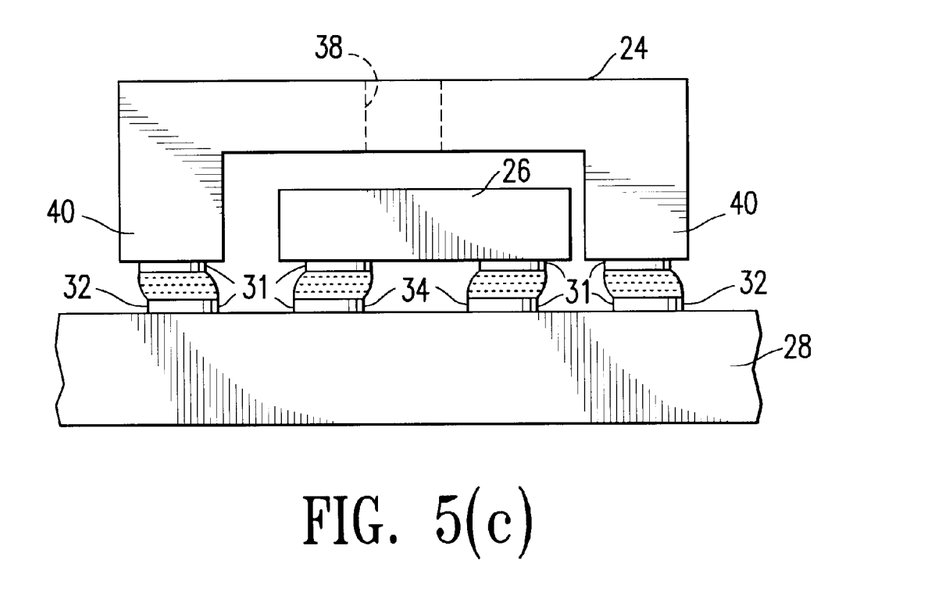
FIG. 5(c) is an exploded top view of the exploded portion shown in FIG. 2 and showing the final connection after the solder bumps have solidified.
Figure 5D:
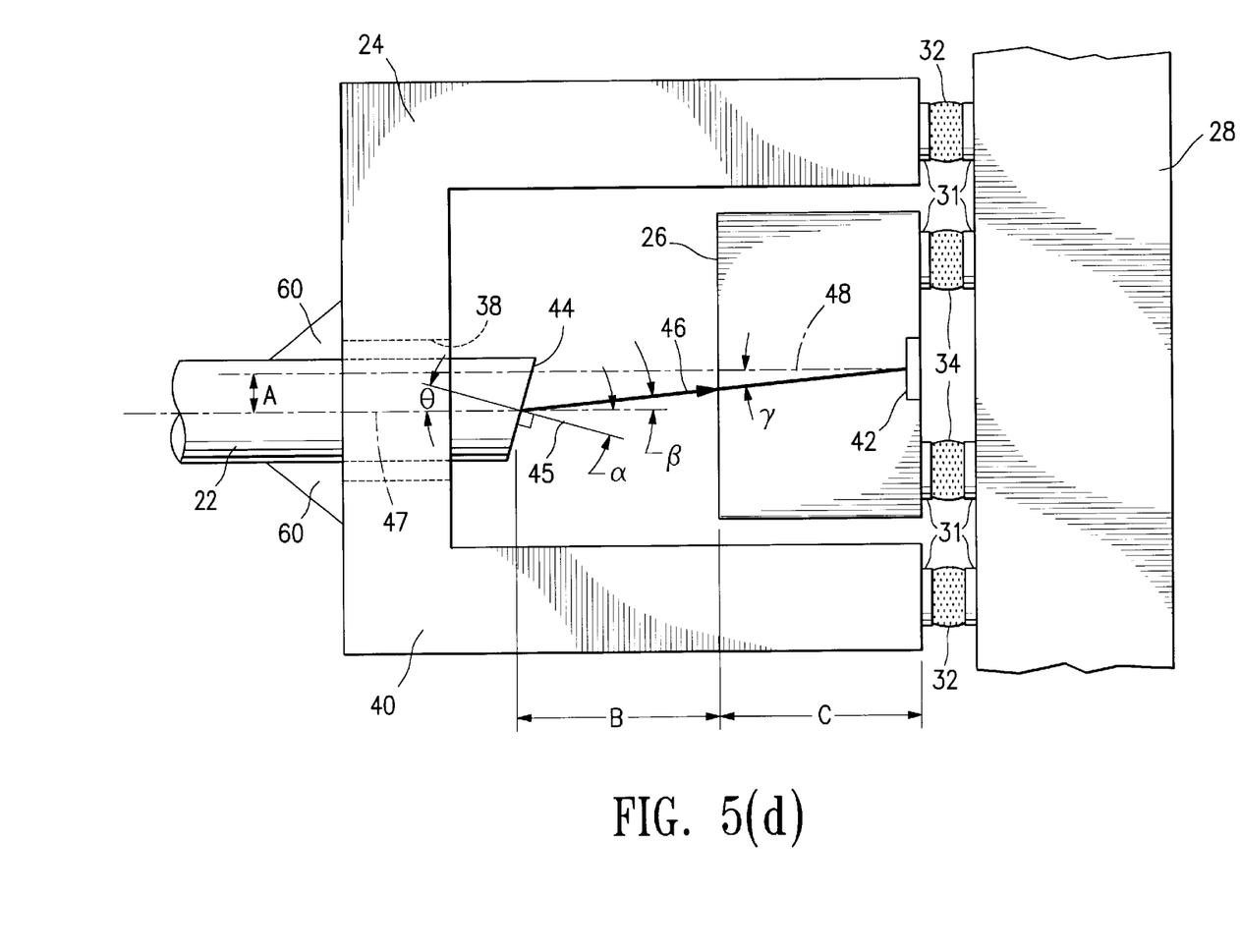
FIG. 5(d) is a cutaway side view illustrating the optical path through the preferred embodiment of the present invention.

The preferred alignment of fiber mount assembly 24 and an avalanche photodiode optical device 26 with optical device mount assembly 28 is shown in FIG. 5(c), although this alignment may vary depending upon the optical device used in the present invention. Alignment may be adjusted by providing opening 38, as shown in FIG. 4(b), at different locations in fiber mount assembly 24. As shown in FIG. 5(d), optical fiber 22 is inserted into opening 38 of fiber mount assembly 24 and is permanently affixed thereto via an adhesive epoxy 60. Avalanche photodiode 26 includes an InGaAs absorption region 42 whose center line 48 is offset a distance A from a center line 47 of optical fiber 22, wherein A is preferably four microns. One surface of avalanche photodiode 26 is provided a distance B from the center of an end portion 44 of optical fiber 22, wherein B is preferably twenty-three microns, and avalanche photodiode 26 preferably has a thickness C of one-hundred microns. End portion 44 of optical fiber 22 is slightly angled so that a line 45 drawn perpendicular to end portion 44 is at an angle θ of preferably eight degrees from center line 47 of optical fiber 22. Line 45 is provided at an angle α of preferably twelve degrees from center line 47 of optical fiber 22. Light 46 exits optical fiber 22 at an angle β of preferably four degrees from center line 47 of optical fiber 22. The path of light 46 is also at an angle γ of preferably 1.35 degrees from center line 48 of InGaAs absorption region 42. Depending upon the properties of optical device 26, these parameters may vary. However, to provide proper alignment of optical fiber 22 with optical device 26, the following equations typically hold true:

$$\sin \alpha / \sin \theta = 1.5$$

$$\sin \beta / \sin \gamma = 3.0$$

The apparatus and method for aligning an optical fiber with an optical device of the present invention provides a simple alignment system without the need for expensive, high-tolerance components. The present invention eliminates capital investment in light sources, measurement instruments, laser welding equipment, motion-controlled positioning stages, and alignment software. The present invention also avoids the conventional peak-power search alignment method, which is very time consuming. Furthermore, the apparatus and method of the present invention consistently and accurately aligns the optical fiber with the optical device.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An apparatus for aligning an optical fiber with an optical device having a first plurality of bond pads provided thereon, the apparatus comprising:

a fiber mount assembly having a body portion with an opening provided therein to receive the optical fiber, and two leg portions integrally connecting to and extending from the body portion, the two leg portions having a second plurality of bond pads provided thereon; and an optical device mount assembly having a third plurality of bond pads provided thereon, and a plurality of eutectic solder bumps provided on the third plurality of bond pads for connecting the first plurality of bond pads of the optical device and the second plurality of bond pads of the two leg portions of the fiber mount assembly to the optical device mount assembly, wherein the concentration of a component of the eutectic material in the plurality of eutectic solder bumps is increased, via a reaction between the first, second and third pluralities of bond pads and the plurality of eutectic solder bumps, until the eutectic material hardens and rigidly connects the first plurality of bond pads of the optical device and second plurality of bond pads of the two leg portions of the fiber mount assembly to the third plurality of bond pads of the optical device mount assembly, aligning the optical fiber with the optical device.

2. An apparatus for aligning an optical fiber with an optical device as recited in claim 1, wherein the optical device comprises an avalanche photodiode having a silicon multiplication and an indium gallium arsenide (InGaAs) absorption region.

3. An apparatus for aligning an optical fiber with an optical device as recited in claim 1, wherein each of the first, second and third pluralities of bond pads comprises a titanium/platinum/gold (Ti/Pt/Au) alloy.

4. An apparatus for aligning an optical fiber with an optical device as recited in claim 3, wherein the Ti/Pt/Au alloy comprises a one-thousand angstrom thick layer of titanium (Ti), a two-thousand angstrom thick layer of platinum (Pt), and a five-thousand angstrom thick layer of gold (Au).

5. An apparatus for aligning an optical fiber with an optical device as recited in claim 3, wherein each of the plurality of eutectic solder bumps comprises a gold/tin (Au/Sn) alloy.

6. An apparatus for aligning an optical fiber with an optical device as recited in claim 5, wherein the Au/Sn alloy comprises eighty percent gold (Au) by weight and twenty percent tin (Sn) by weight.

7. A method for aligning an optical fiber with an optical device, the method comprising the steps of:

providing a plurality of eutectic solder bumps on a first plurality of bond pads provided on an optical device mount assembly;

contacting a second plurality of bond pads provided on two leg portions of a fiber mount assembly with some of the plurality of eutectic solder bumps, the fiber mount assembly having a body portion with an opening provided therein, wherein the two leg portions integrally connect to and extend from the body portion;

contacting a third plurality of bond pads provided on the optical device with the remaining plurality of eutectic solder bumps provided on the first plurality of bond pads of the optical device mount assembly;

increasing the concentration of a component of the eutectic material in the plurality of eutectic solder bumps, via a reaction between the first, second and third pluralities of bond pads and the plurality of eutectic solder bumps, until the eutectic material hardens and rigidly connects the third plurality of bond pads of the optical device and the second plurality of bond pads of the two leg portions of the fiber mount assembly to the first plurality of bond pads of optical device mount assembly, aligning the optical fiber with the optical device; and providing the optical fiber through the opening provided in the body portion of the fiber mount assembly.

8. A method for aligning an optical fiber with an optical device as recited in claim 7, wherein the optical device comprises an avalanche photodiode having a silicon multiplication and an indium gallium arsenide (InGaAs) absorption region.

9. A method for aligning an optical fiber with an optical device as recited in claim 7, wherein each of the first, second and third pluralities of bond pads comprises a titanium/platinum/gold (Ti/Pt/Au) alloy.

10. A method for aligning an optical fiber with an optical device as recited in claim 9, wherein the Ti/Pt/Au alloy comprises a one-thousand angstrom thick layer of titanium (Ti), a two-thousand angstrom thick layer of platinum (Pt), and a five-thousand angstrom thick layer of gold (Au).

11. A method for aligning an optical fiber with an optical device as recited in claim 9, wherein each of the plurality of eutectic solder bumps comprises a gold/tin (Au/Sn) alloy.

12. A method for aligning an optical fiber with an optical device as recited in claim 11, wherein the Au/Sn alloy comprises eighty percent gold (Au) by weight and twenty percent tin (Sn) by weight.

* * * * *